(12) United States Patent
Surtees et al.

(10) Patent No.: US 12,256,970 B2
(45) Date of Patent: Mar. 25, 2025

(54) CARBON DIOXIDE-BASED PERCUTANEOUS CRYOSURGICAL SYSTEM

(71) Applicant: THE JOHNS HOPKINS UNIVERSITY, Baltimore, MD (US)

(72) Inventors: Bailey Surtees, Edmond, OK (US); Evelyn McChesney, Baltimore, MD (US); Sean Young, Baltimore, MD (US); Yixin Hu, Baltimore, MD (US); Nicholas James Durr, Baltimore, MD (US); Tara Blair, Baltimore, MD (US); Pascal Acree, Baltimore, MD (US); Grace Kuroki, Baltimore, MD (US); Susan C. Harvey, Lutherville, MD (US); Serena M. Thomas, Summit, NJ (US)

(73) Assignee: The Johns Hopkins University, Baltimore, MD (US)

( * ) Notice: Subject to any disclaimer, the term of this patent is extended or adjusted under 35 U.S.C. 154(b) by 692 days.

(21) Appl. No.: 17/052,450

(22) PCT Filed: May 1, 2019

(86) PCT No.: PCT/US2019/030126
§ 371 (c)(1),
(2) Date: Nov. 2, 2020

(87) PCT Pub. No.: WO2019/213205
PCT Pub. Date: Nov. 7, 2019

(65) Prior Publication Data
US 2021/0169546 A1    Jun. 10, 2021

Related U.S. Application Data

(60) Provisional application No. 62/664,998, filed on May 1, 2018.

(51) Int. Cl.
*A61B 18/02* (2006.01)
*F25B 19/00* (2006.01)
*A61B 90/00* (2016.01)

(52) U.S. Cl.
CPC ............ *A61B 18/02* (2013.01); *F25B 19/005* (2013.01); *A61B 2018/0262* (2013.01); *A61B 2018/0293* (2013.01); *A61B 2090/378* (2016.02)

(58) Field of Classification Search
CPC .......... A61B 18/02; A61B 2018/00333; A61B 2018/0262; A61B 2018/0293
See application file for complete search history.

(56) References Cited

U.S. PATENT DOCUMENTS

| 1,780,267 A | 8/1928 | Young |
| 3,266,492 A | 8/1966 | Steinberg |

(Continued)

FOREIGN PATENT DOCUMENTS

| AU | 2005218066 A1 | 11/2005 |
| EP | 1347261 B1 | 9/2003 |

(Continued)

OTHER PUBLICATIONS

Extended European Search Report for Application No. EP19797090.8, mailed on Dec. 23, 2021, 9 pages.

(Continued)

*Primary Examiner* — Daniel W Fowler
(74) *Attorney, Agent, or Firm* — Harrity & Harrity, LLP

(57) ABSTRACT

An embodiment in accordance with the present invention provides a handheld cryoprobe for use in percutaneous cryotherapy of tumorous masses. It includes a probe attached to a $CO_2$ gas dispensing backend. The probe has specifically optimized parameters designed for use with $CO_2$ gas and is made out of a partially hollowed and threaded (Continued)

aluminum rod providing maximum heat exchange. The system backend regulates flow of compressed $CO_2$ gas while throttling and cooling the gas coolant to the cytotoxically low temperatures necessary for targeted tumor cell death. Additionally, the incoming initial stream of $CO_2$ gas is throttled by the Joule-Thomson nozzle on the backend. The low temperature exhaust gas is then used to pre-cool all subsequent incoming gas, resulting in an even lower temperature at the probe tip, which provides a positive feedback loop, continually decreasing the gas's temperature. The temperature drop is caused by the Joule-Thomson effect.

20 Claims, 10 Drawing Sheets

(56) References Cited

U.S. PATENT DOCUMENTS

| | | | |
|---|---|---|---|
| 3,272,203 A | 9/1966 | Chato | |
| 3,298,371 A | 1/1967 | Lee | |
| 3,343,544 A * | 9/1967 | Dunn | A61B 18/02 606/26 |
| 3,575,176 A * | 4/1971 | Crump | A61B 18/02 606/26 |
| 3,696,813 A * | 10/1972 | Wallach | F25B 9/02 606/26 |
| 3,850,741 A | 11/1974 | Callahan et al. | |
| 3,910,277 A | 10/1975 | Zimmer | |
| 3,911,924 A | 10/1975 | Zimmer | |
| 3,948,269 A | 4/1976 | Zimmer | |
| 3,971,383 A | 7/1976 | van Gerven | |
| 4,116,199 A * | 9/1978 | Bryne | A61B 18/0218 606/22 |
| 4,211,231 A * | 7/1980 | Rzasa | A61B 18/0218 606/26 |
| 5,108,390 A * | 4/1992 | Potocky | A61B 18/02 606/21 |
| 5,758,505 A | 6/1998 | Dobak, III et al. | |
| 5,759,182 A * | 6/1998 | Varney | A61B 18/02 607/104 |
| 5,885,276 A * | 3/1999 | Ammar | A61B 18/02 606/22 |
| 6,270,476 B1 * | 8/2001 | Santoianni | A61M 25/0147 604/95.04 |
| 6,494,844 B1 | 12/2002 | Van Bladel et al. | |
| 6,585,728 B2 | 7/2003 | Heiner et al. | |
| 6,767,346 B2 | 7/2004 | Damasco et al. | |
| 6,878,149 B2 | 4/2005 | Gatto | |
| 7,846,154 B2 | 12/2010 | Bliweis et al. | |
| 8,298,220 B2 | 10/2012 | Devens, Jr. et al. | |
| 8,591,505 B2 | 11/2013 | Sharon et al. | |
| 8,845,627 B2 | 9/2014 | George et al. | |
| 9,598,124 B2 | 3/2017 | Friesen | |
| 2002/0022832 A1 | 2/2002 | Mikus et al. | |
| 2004/0210212 A1 | 10/2004 | Maurice | |
| 2004/0215295 A1 | 10/2004 | Littrup et al. | |
| 2005/0038422 A1 * | 2/2005 | Maurice | A61B 18/02 606/23 |
| 2007/0149958 A1 | 6/2007 | Delonzor et al. | |
| 2007/0149959 A1 | 6/2007 | DeLonzor et al. | |
| 2008/0027419 A1 * | 1/2008 | Hamel | A61B 18/02 606/20 |
| 2008/0027420 A1 * | 1/2008 | Wang | A61B 18/02 606/21 |
| 2008/0051776 A1 * | 2/2008 | Bliweis | A61B 18/02 606/21 |
| 2008/0110182 A1 * | 5/2008 | Vancelette | A61B 18/02 62/50.7 |
| 2008/0114347 A1 | 5/2008 | Devens et al. | |
| 2008/0255551 A1 * | 10/2008 | DeLonzor | A61B 18/02 606/22 |
| 2010/0152722 A1 | 6/2010 | Kleinberger | |
| 2013/0331829 A1 | 12/2013 | Babkin et al. | |
| 2014/0275767 A1 | 9/2014 | Baust | |
| 2016/0120523 A1 | 5/2016 | Yarmus | |

FOREIGN PATENT DOCUMENTS

| | | |
|---|---|---|
| EP | 1333759 B1 | 4/2010 |
| EP | 2311398 A1 | 4/2011 |
| WO | 1999065410 A1 | 12/1999 |

OTHER PUBLICATIONS

International Search Report and Written Opinion for Application No. PCT/US2019/030126 mailed on Aug. 22, 2019, 6 pages.

* cited by examiner

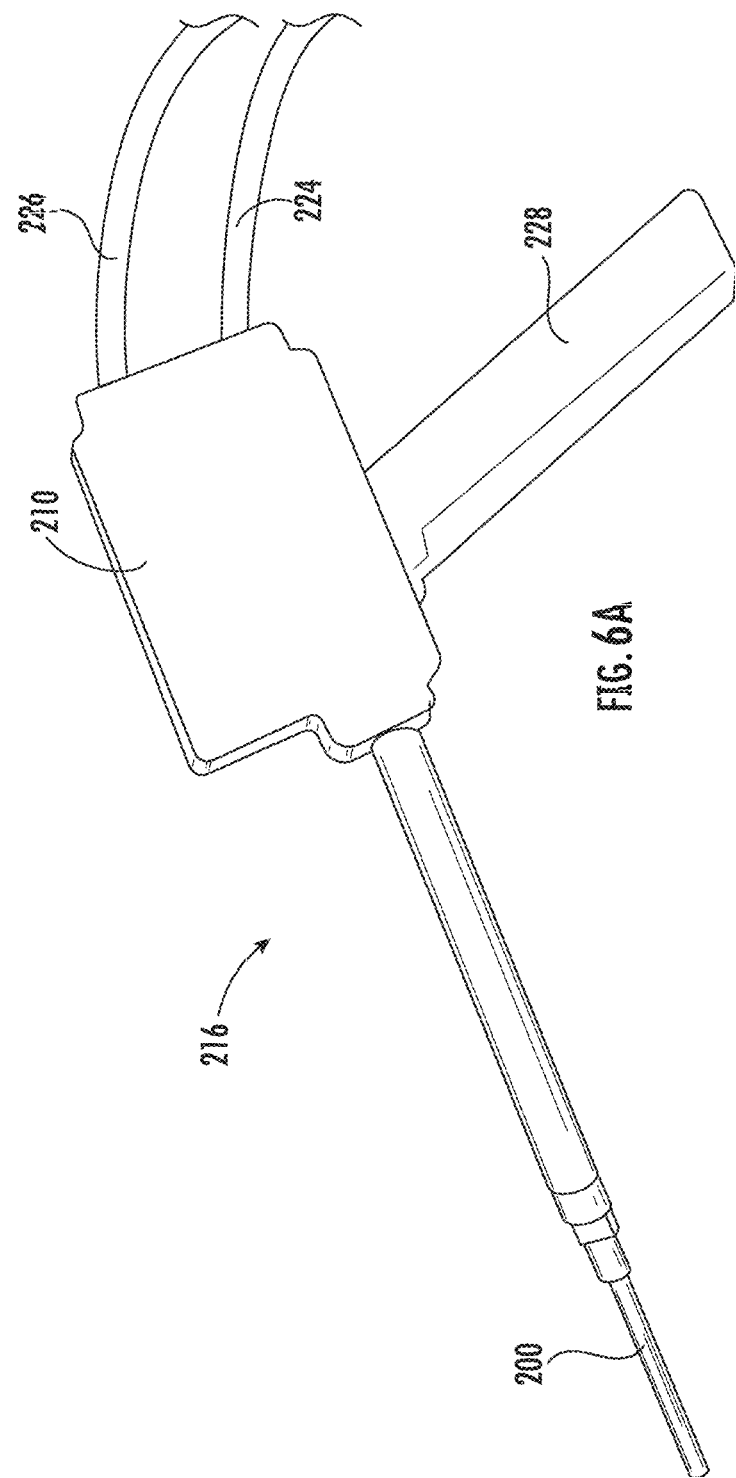

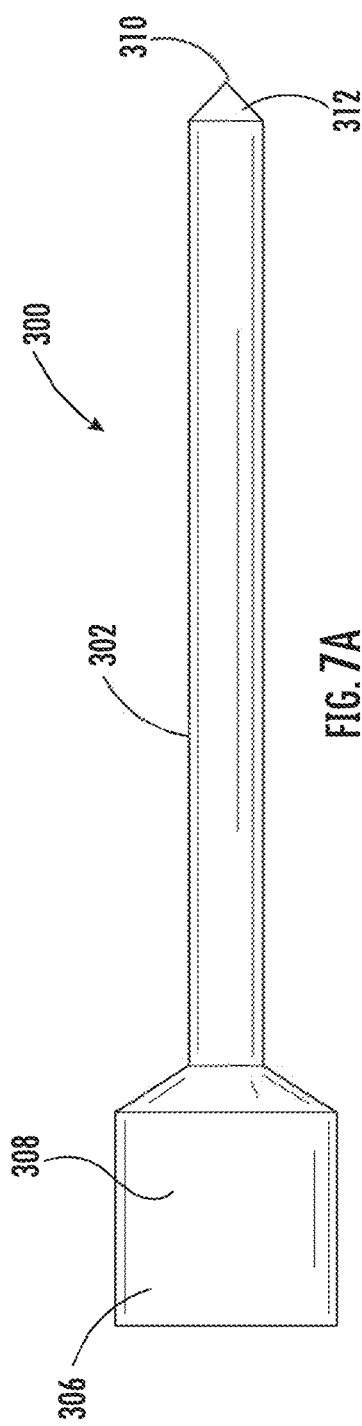
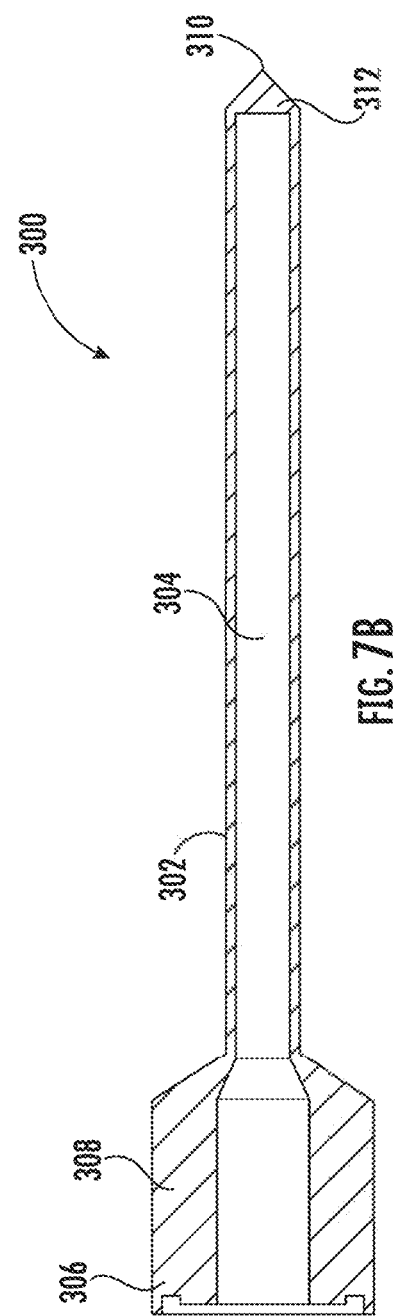

CARBON DIOXIDE-BASED PERCUTANEOUS CRYOSURGICAL SYSTEM

CROSS-REFERENCE TO RELATED APPLICATIONS

This application is a 35 U.S.C. § 371 U.S. national entry of International Application PCT/US2019/030126, having an international filing date of May 1, 2019, which claims the benefit of U.S. Provisional Application No. 62/664,998, filed May 1, 2018, the content of each of the aforementioned applications is herein incorporated by reference in its entirety.

FIELD OF THE INVENTION

The present invention relates generally to medical devices. More particularly, the present invention relates to a carbon dioxide-based percutaneous cryosurgical system.

BACKGROUND OF THE INVENTION

Cryotherapy treatment can be effective for treatment of cancer and other pathologies in humans and animals. However, this form of treatment can often been very expensive for the developing world and the veterinary markets where it is used. One driver of the high cost of this treatment is that expensive gas is often used to provide the cooling associated with the cryotherapy.

Therefore, it would be advantageous to provide a carbon dioxide-based percutaneous cryosurgical system for effective treatment and reduced cost.

SUMMARY OF THE INVENTION

The foregoing needs are met, to a great extent, by the present invention, wherein in one aspect a device for cryotherapy includes a probe having an outer surface defining an inner lumen. The device includes a backend component configured to be coupled to the probe. The backend component is configured to be connected to a source of carbon dioxide gas. The backend component includes a lever to enable dispensing the carbon dioxide gas. The device also includes a Joule-Thomson nozzle disposed within the backend component, such that the carbon dioxide gas is throttled to decrease a temperature of the carbon dioxide gas.

In accordance with an aspect of the present invention, the device further includes a flow path for carbon dioxide gas from the backend, into the inner lumen of the probe and back out through the backend component. The device includes a source of carbon dioxide gas. The source of carbon dioxide gas takes the form of a conventional carbon dioxide gas tank. The device includes a flange for coupling the probe to the backend component. The backend component includes a vent for venting spent carbon dioxide gas. The backend component includes tubing for coupling to a source of carbon dioxide gas. The shape of the probe is optimized for cryotherapy. The shape of the probe is configured for formation of an ice ball for delivery of cryotherapy. The device further includes an ultrasound component for monitoring cryotherapy treatment.

In accordance with another aspect of the present invention, a method of cryotherapy includes providing a flow path for directing $CO_2$ gas from a room temperature tank into a backend component of a device through gas inflow tubing, into a treatment probe, and back into the backend component. The flow path is configured for throttling the gas through a Joule-Thomson nozzle to rapidly cool the gas. The flow path is also configured for flowing the gas into a probe of the device to allow for treatment and exiting the gas from the probe, such that the gas flows back through the backend component of the device. Further, the flow path is configured for venting the gas from the backend component of the device.

In accordance with still another aspect of the present invention, the gas flow can be turned on and off directly at the room temperature tank. Consistent internal pressure is ensured via a regulator. The method includes providing an ultrasound component for monitoring the cryotherapy. The probe is configured for cryotherapy. The method includes optimizing a flow path for the flow of $CO_2$. In addition, the method includes generating a freeze-thaw-freeze cycles are used to freeze a tumor. The probe is configured to be inserted percutaneously. The method includes providing a flange for coupling the probe to the backend of the device. The method also provides for rapidly cooling the gas to −50° C.

BRIEF DESCRIPTION OF THE DRAWINGS

The accompanying drawings provide visual representations, which will be used to more fully describe the representative embodiments disclosed herein and can be used by those skilled in the art to better understand them and their inherent advantages. In these drawings, like reference numerals identify corresponding elements and:

FIGS. 6A-6C illustrate side and sectional views of a cryotherapy device, according to an embodiment of the present invention.

FIGS. 7A and 7B illustrate side and sectional views of a probe tip, according to an embodiment of the present invention.

DETAILED DESCRIPTION

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

An embodiment in accordance with the present invention provides a handheld cryoprobe for use in percutaneous cryotherapy of tumorous masses in the body. Cryotherapy includes any treatment with cold temperature known to or conceivable to one of skill in the art. The device includes a probe attached to a $CO_2$ gas dispensing system backend. The probe has specifically optimized parameters designed for use with $CO_2$ gas and is made out of a partially hollowed and threaded aluminum rod of a specific shape, providing maximum heat exchange. The system backend regulates the flow of compressed $CO_2$ gas while throttling and cooling the gas coolant to the cytotoxically low temperatures necessary for targeted tumor cell death. Additionally, the incoming initial stream of $CO_2$ gas is throttled by the Joule-Thomson nozzle on the backend to further cool the probe. The low temperature exhaust gas is then used to pre-cool all subsequent incoming gas, resulting in an even lower temperature at the probe tip. This provides a positive feedback loop which is continually decreasing the temperature of the gas. The temperature drop is caused by the Joule-Thomson effect. Using a combination of this precooling heat exchange and the heat exchange in the probe due to the Joule Thomson effect, the probe tip is cooled and produces an ice ball around the cryoprobe.

The present invention is optimized for $CO_2$ at the moment because of its availability and low cost. Other high-end systems typically use costly gases, like nitrogen or argon, which cool to lower temperatures at faster rates but have limited availability for many parts of the world. This handheld system is made specifically to work with $CO_2$ because it is able to achieve the desired results of cooling human tissue and forming an ice ball around a mass while being usable worldwide.

Figure 1:
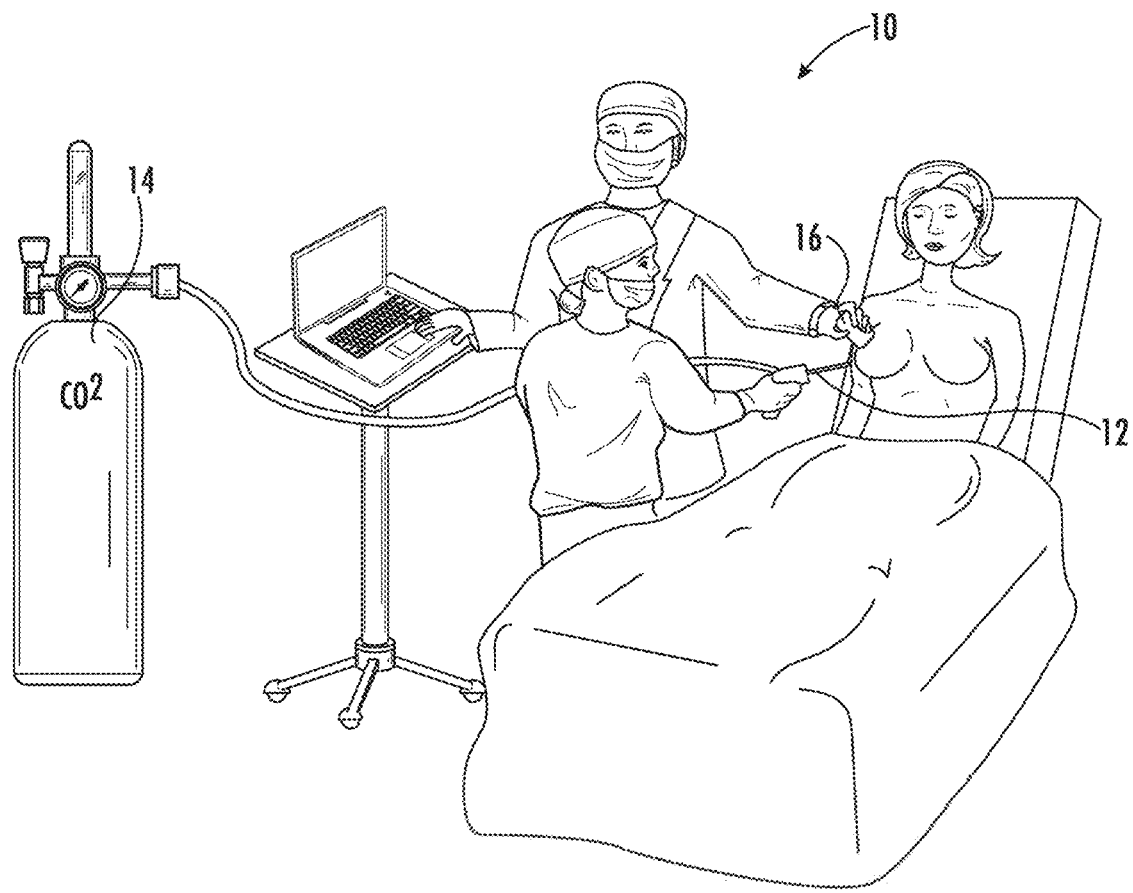
FIG. 1 illustrates a perspective view of a cryoprobe according to the present invention being used in a surgical setting.

FIG. 1 illustrates a perspective view of a cryoprobe according to the present invention being used in a surgical setting. As illustrated in FIG. 1, the system 10 of the present invention includes a cryoprobe 12 and a source of $CO_2$ 14. The source of $CO_2$ 14 can take the form of a portable gas tank, or any other suitable source of $CO_2$ known to or conceivable to one of skill in the art. In some embodiments, ultrasound 16 is used to locate the tumor for treatment. After the tumor is located, the cryoprobe 12 is inserted into the tumor. $CO_2$ flow is then initiated. In a preferred embodiment, freeze-thaw-freeze cycles are used to freeze the tumor. Tumor growth is monitored with the ultrasound 16. Finally, the cryoprobe 12 is removed and the necrosed tumor is left behind.

Figure 2:
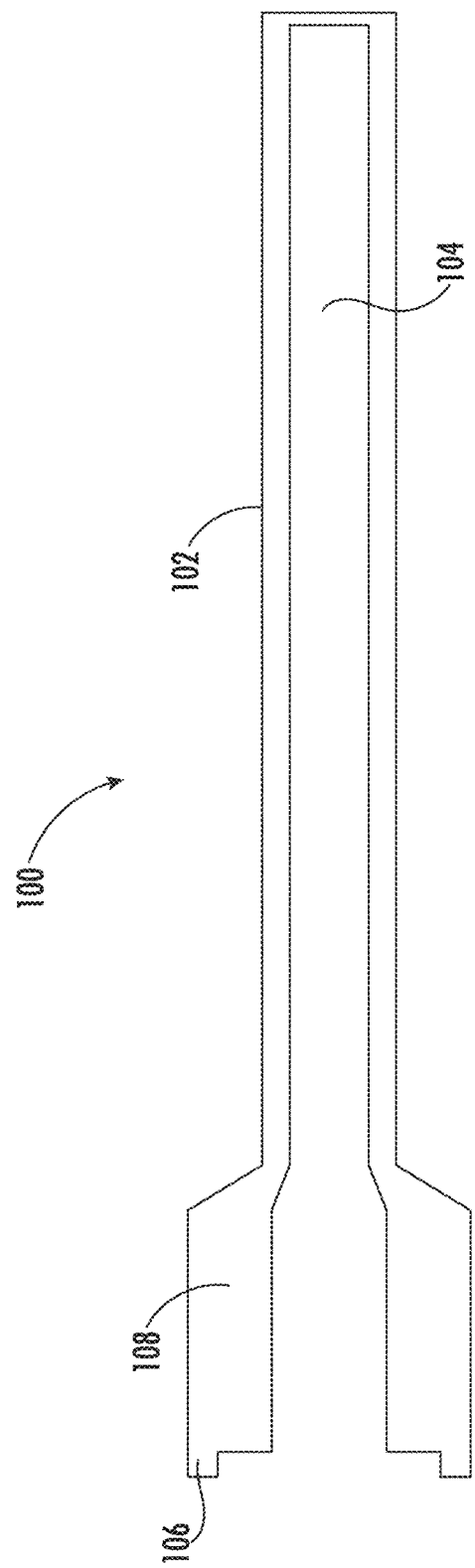
FIG. 2 illustrates a sectional view of a distal probe, according to an embodiment of the present invention.

FIG. 2 illustrates a sectional view of a distal probe, according to an embodiment of the present invention. The probe 100 is configured for insertion into the tumor, where it acts like a heat exchanger freezing the tissue into which it is inserted. The probe 100 includes a shaft 102 defining a lumen 104 through which the $CO_2$ flows. A proximal end 106 of the probe 100 includes a flange 108 which allows for coupling with the backend component of the cryoprobe, described further herein. The optimized dimensions shown in FIG. 2 provide maximum heat exchange with the use of $CO_2$. This differs from previous cryoprobes because the state of the art for percutaneous cryosurgery is use of nitrogen or argon as the coolant. Therefore, the optimization of the device to allow for effective use with $CO_2$ is not shown in the prior art.

Figure 3:
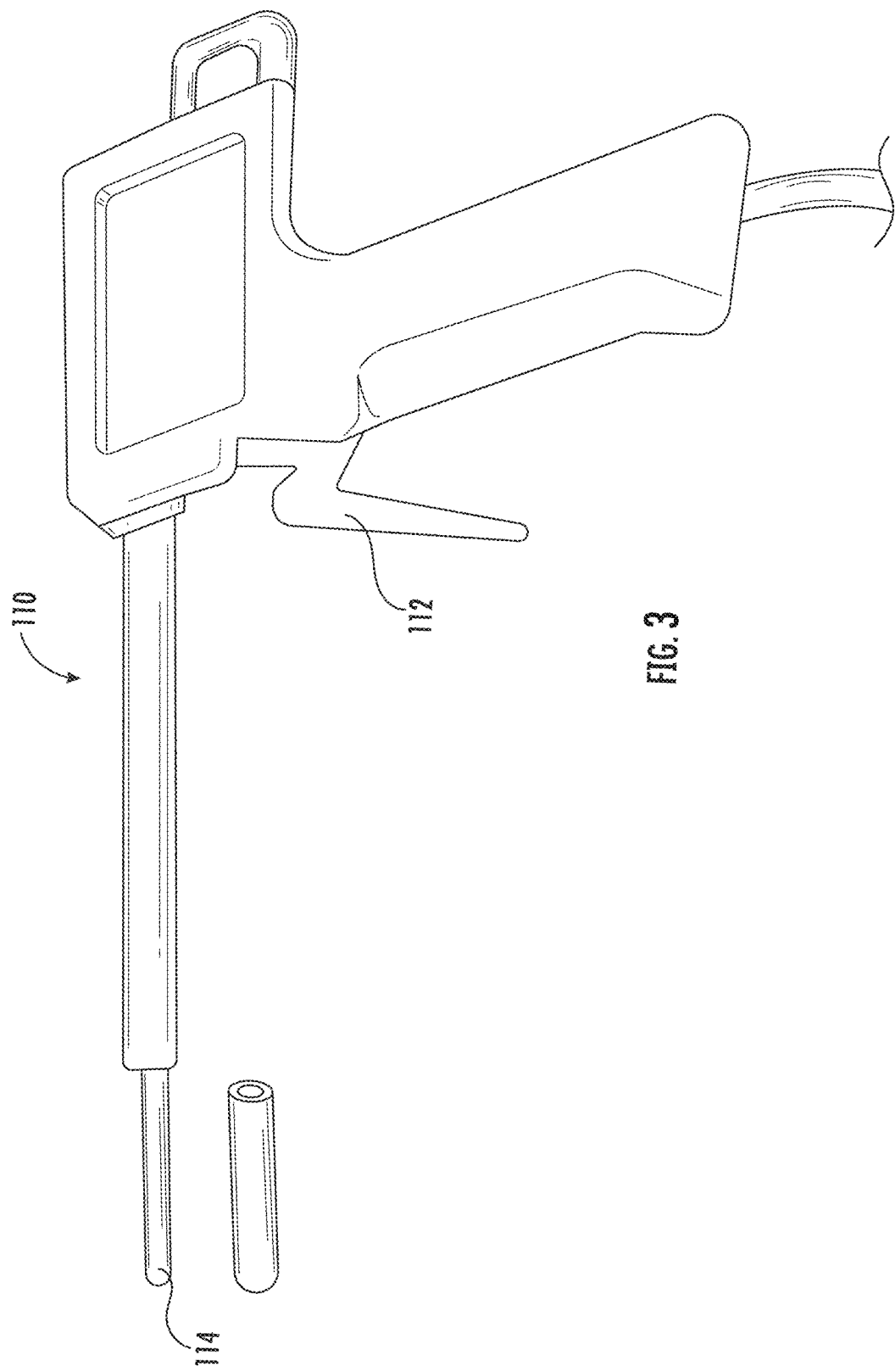
FIG. 3 illustrates a side view of a backend component of the cryoprobe, according to an embodiment of the present invention.
Figure 4:
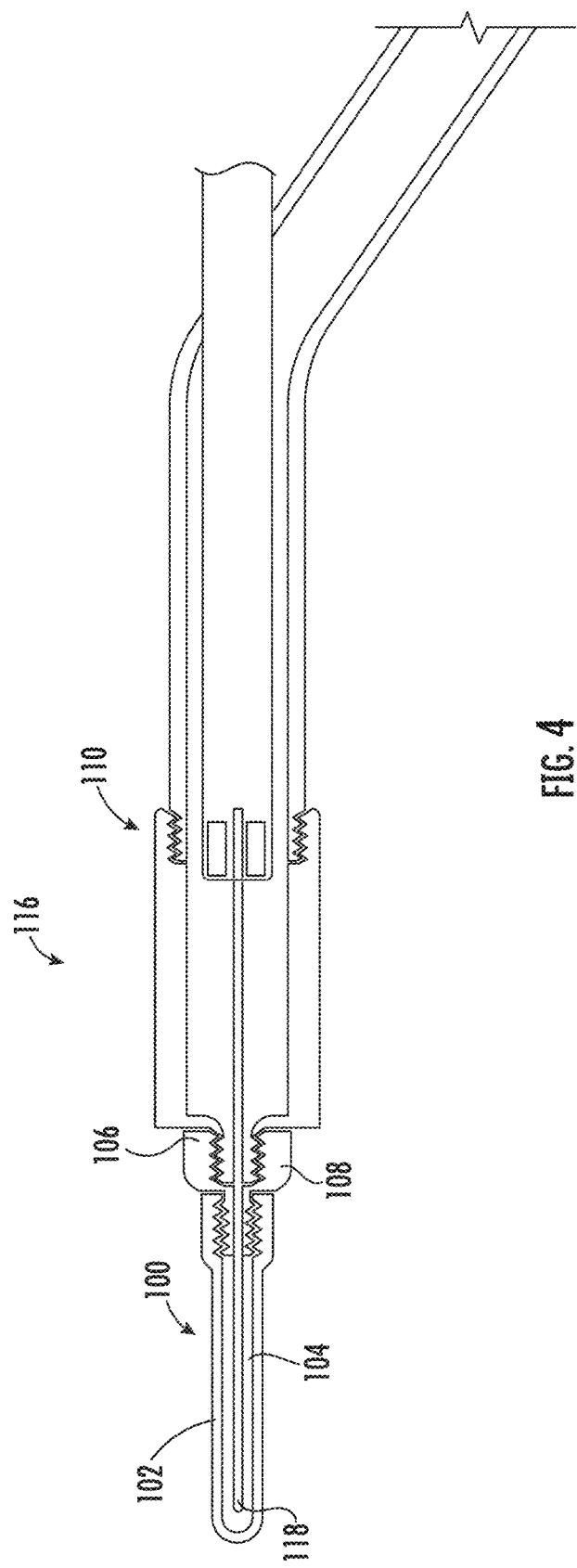
FIGS. 4, 5A, and 5B illustrate a sectional view of a cryoprobe according to an embodiment of the present invention.
Figure 5A:
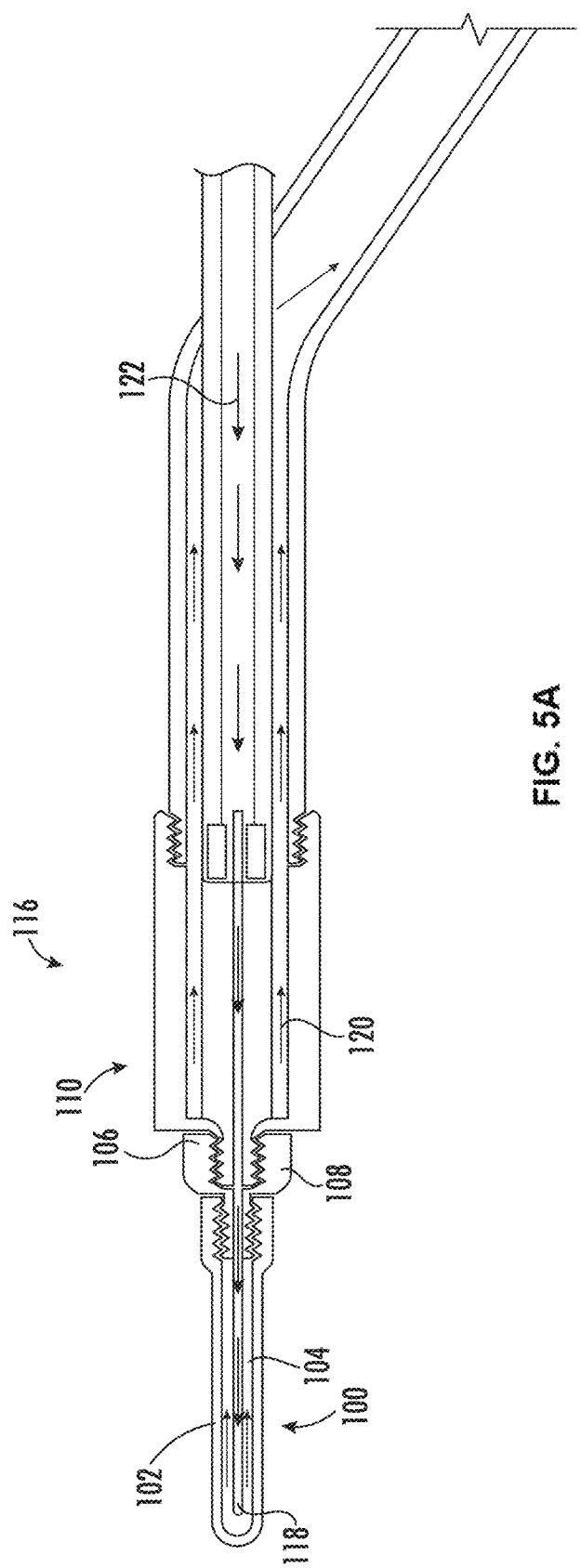
Figure 5B:
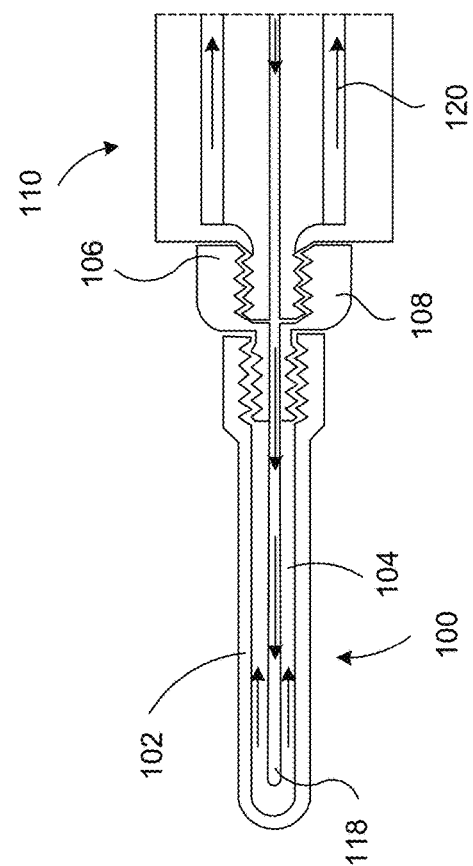

FIG. 3 illustrates a side view of a backend component of the cryoprobe, according to an embodiment of the present invention. The backend component 110 of the cryoprobe supplies compressed gas from the $CO_2$ tank to the probe. The backend component 110 rapidly cools the $CO_2$ gas and uses exhausted gas to precool the incoming gas to allow for more efficient and effective cooling with the $CO_2$ gas. The backend component includes a lever 112 for engaging flow of $CO_2$ gas. While a lever is shown in FIG. 2, it is not necessary in all embodiments of the present invention, as will be further illustrated herein. The flow of gas can be engaged in any way known to or conceivable by one of skill in the art. The backend component 110 also includes a coupling 114 for adding the probe described in FIG. 2. FIGS. 4 and 5 illustrate a sectional view of a cryoprobe, according to an embodiment of the present invention. FIGS. 4 and 5 illustrate the cryoprobe 116 which includes the probe 100 and the backend component 110. Gas flows from the room temperature tank into the backend component 110. The gas can flow through tubing connecting the gas tank to the backend component. The gas is throttled by the Joule-Thomson nozzle 118 rapidly cooling the gas from 23 to −50° C. The extremely cold gas 120 flows into the lumen 104 of the probe 100 for cooling that can be directed to treatment. The extremely cold gas 120 then exits the probe and flows back through the backend component 110 from which it is vented out to atmosphere. As the extremely cold gas 120 flows back through the backend component 110, this extremely cold gas 120 interfaces with the inflow tube, precooling new gas 122 and creating a positive feedback loop to allow the gas and thereby the device to reach temperatures cool enough for effective treatment.

Further, an inner lumen of the probe, preferably, is formed from a material with sufficiently high thermal conductivity, such that heat transfer occurs between incoming room-temperature gas and outflowing low-temperature gas so as to pre-cool the incoming gas to further decrease the temperature within the probe, such as, but not limited to, aluminum or stainless steel. A portion of the precooling of the incoming gas occurs within the body contained within the probe. The probe and the backend component are preferably formed from materials that can be sterilized and reused with a solution of bleach and water, ethylene oxide gas, steam sterilization, or any other form of sterilization known to or conceivable to one of skill in the art. In some embodiments, the probe can be removed from the backend component and sterilized or autoclaved separately from the backend of the device. In some embodiments, the probe can include at least a partial cover formed from a material with poor thermal heat transfer, thereby limiting and focusing tissue damage along a length of the probe.

Figure 6B:
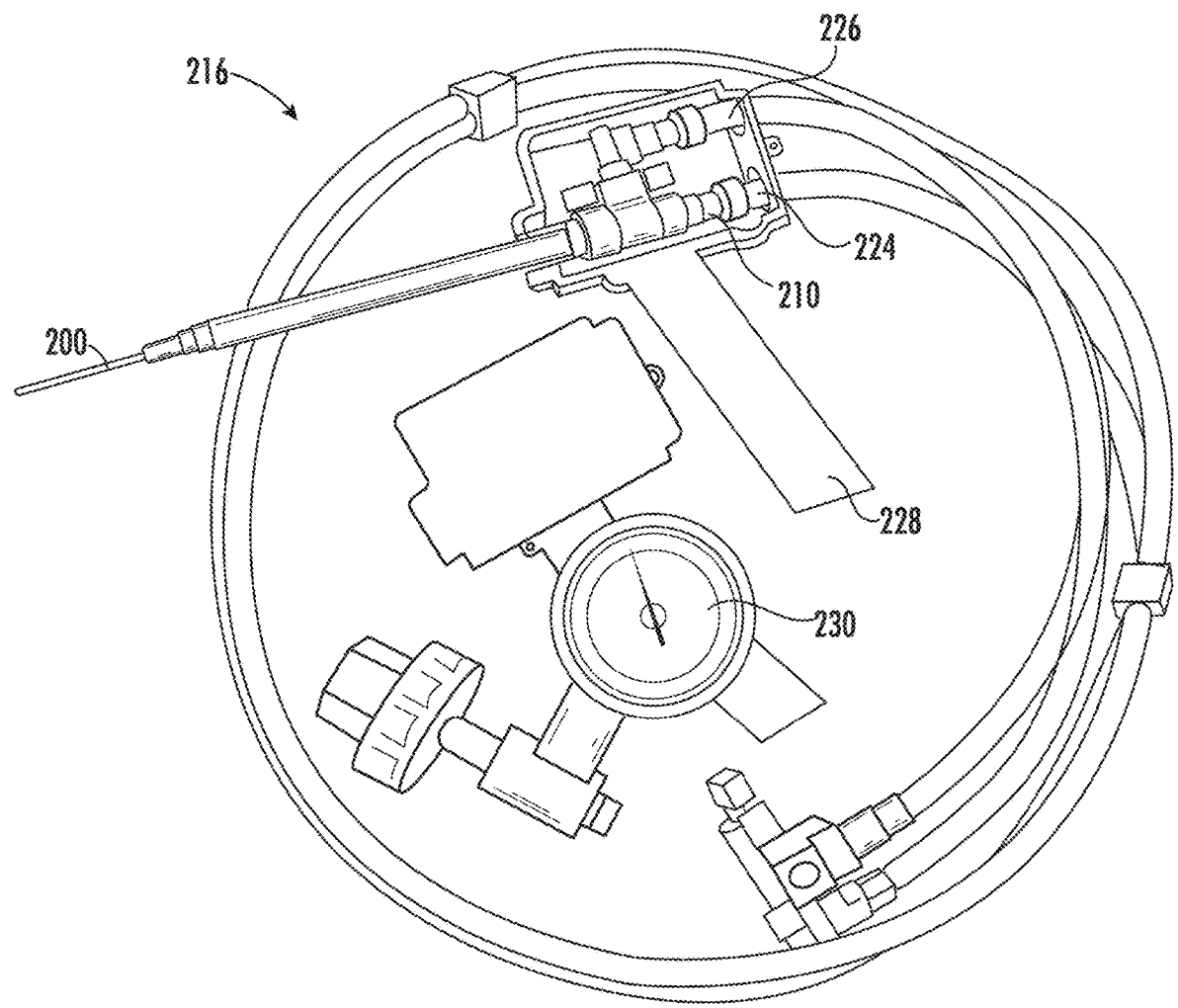
Figure 6C:
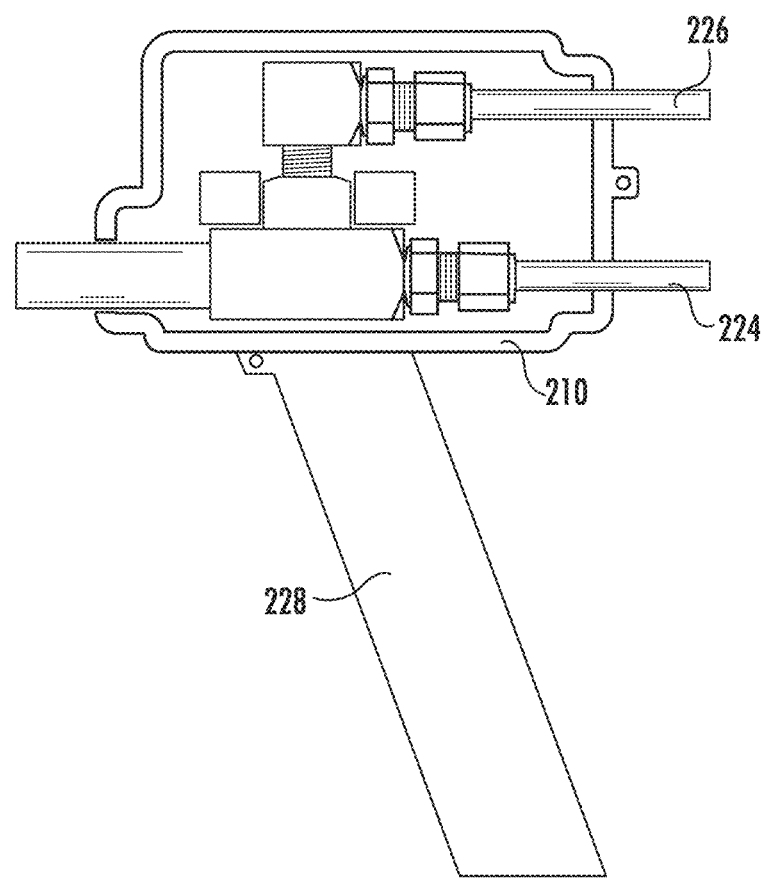

FIGS. 6A-6C illustrate side and sectional views of a cryotherapy device, according to an embodiment of the present invention. FIGS. 6A-6C illustrate the cryoprobe 216 which includes the probe 200 and the backend component 210. Gas flows from the room temperature tank into the backend component 210 through gas inflow tubing 224. The gas can flow through tubing 224 connecting the gas tank to the backend component. The gas is throttled by the Joule-Thomson nozzle (not pictured) rapidly cooling the gas from 23 to −50° C. The extremely cold gas flows into the probe 200 for cooling that can be directed to treatment. The extremely cold gas then exits the probe 200 and flows back through the backend component 210 from which it is vented out of a vent tube 226. Gas flow is turned on and off directly at the tank. The backend component can also include handle 228. The handle 228 can be attached proximal to the junction of probe 200 and backend 210 for ease of operability. The handle 228 is made from sufficiently insulating materials so as to protect the operator's hand from experiencing any cooling. The handle 228 is removable such that the rest of the device may be cleaned separately. The backend component can also include a regulator 230 to ensure consistent internal pressure.

FIGS. 7A and 7B illustrate side and sectional views of a probe tip, according to an embodiment of the present invention. The probe 300 is configured for insertion into the tumor, where it acts like a heat exchanger freezing the tissue into which it is inserted. The probe 300 includes a shaft 302 defining a lumen 304 through which the $CO_2$ flows. A proximal end 306 of the probe 300 includes a flange 308 which allows for coupling with the backend component of the cryoprobe. The flange 308 can be threaded for easy removal, or exchange of different probes during a procedure. A distal end 310 of the probe 300 includes a cone-shaped tip 312. The cone-shaped, pointed tip is optimized for use with $CO_2$. The cone-shaped, pointed tip is ideal for cryotherapy done percutaneously. It is also possible in some embodiments that multiple probes or a probe with multiple tips can also be used.

In some embodiments, the device of the present invention can include a warming device immediately proximal to the point of connection for the probe. This can help to keep healthy tissue at a proper temperature. The warming device can take the form of a closed material through which water can circulate, a warming blanket or heating pad, or any other means of warming known to or conceivable to one of skill in the art.

Control of the present invention can in some embodiments be carried out using a computer, non-transitory computer readable medium, or alternately a computing device or non-transitory computer readable medium incorporated into the robotic device. A non-transitory computer readable medium is understood to mean any article of manufacture that can be read by a computer. The computing device can include instructions for usage of the carbon dioxide-based percutaneous cryotherapy system. The computing device can also be used for desired treatment placements and times from predefined imaging parameters. The computing device can also be used to process images taken from imaging such as but not limited to ultrasound and further instructs the user on changes in treatment parameters.

Such non-transitory computer readable media includes, but is not limited to, magnetic media, such as a floppy disk, flexible disk, hard disk, reel-to-reel tape, cartridge tape, cassette tape or cards, optical media such as CD-ROM, writable compact disc, magneto-optical media in disc, tape or card form, and paper media, such as punched cards and paper tape. The computing device can be a special computer designed specifically for this purpose. The computing device can be unique to the present invention and designed specifically to carry out the method of the present invention. The operating console for the device is a non-generic computer specifically designed by the manufacturer. It is not a standard business or personal computer that can be purchased at a local store. Additionally, the console computer can carry out communications through the execution of proprietary custom built software that is designed and written by the manufacturer for the computer hardware to specifically operate the hardware.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A device for percutaneous cryotherapy comprising:
a probe comprising an outer surface defining an inner lumen and wherein the probe is configured to be inserted percutaneously;
a backend component configured to be coupled to the probe, wherein the backend component is configured to be connected to a source of carbon dioxide gas;
a Joule-Thomson nozzle disposed within the backend component; and
a flow path configured to direct incoming gas of the carbon dioxide gas to flow through the Joule-Thomson nozzle, out of the Joule-Thomson nozzle, into the inner lumen of the probe, and back out through the backend component via a first area within a first lumen in the backend component and outside of the Joule-Thomson nozzle,
wherein the Joule-Thomson nozzle extends into a second lumen in the backend component and the second lumen is configured to carry the incoming gas from the source of carbon dioxide gas to the Joule-Thomson nozzle,
wherein a first portion of the second lumen extends into the backend component and a second portion of the second lumen extends outside the backend component, and
wherein the second lumen is wider than the Joule-Thomson nozzle,
wherein a first portion of the Joule-Thomson nozzle that extends into the second lumen is surrounded by another material between the first portion of the Joule-Thomson nozzle and the second lumen,
wherein a second portion of the Joule-Thomson nozzle that extends into the second lumen further extends into the second lumen beyond the other material and ends within the second lumen, and
wherein the backend component is further configured to include a choke point portion configured to throttle the incoming gas, flowing from the second lumen and into the Joule-Thomson nozzle, to decrease a temperature of the incoming gas,
wherein the choke point portion is comprised of at least the first portion of the Joule-Thomson nozzle, the second portion of the Joule-Thomson nozzle, the other material, and the first portion of the second lumen, and
wherein the choke point portion throttles the incoming gas via a difference between a first width of the second lumen and a second width of the Joule-Thomson nozzle.

2. The device of claim 1 further comprising a flow path configured to direct the carbon dioxide gas from the backend component and through the Joule-Thomson nozzle.

3. The device of claim 1 further comprising the source of carbon dioxide gas.

4. The device of claim 3 wherein the source of carbon dioxide gas takes a form of a carbon dioxide gas tank.

5. The device of claim 1 wherein the probe comprises a flange for coupling the probe to the backend component.

6. The device of claim 1 wherein the backend component includes a vent for venting spent carbon dioxide gas.

7. The device of claim 1 wherein the backend component comprises tubing for coupling to the source of carbon dioxide gas.

8. The device of claim 1 wherein the probe is configured for formation of an ice ball for delivery of cryotherapy, wherein the ice ball is formed based on the carbon dioxide gas.

9. The device of claim 1 further comprising an ultrasound component for monitoring cryotherapy treatment.

10. The device of claim 1, wherein the flow path is further configured to create a positive feedback loop for cooling subsequent incoming carbon dioxide gas through the backend component, based on the carbon dioxide gas flowing back out.

11. The device of claim 1, wherein a component including the second lumen is configured to attach to the backend component.

12. A method of cryotherapy comprising:
providing a flow path for directing carbon dioxide ($CO_2$) gas from a room temperature tank into a backend component of a device through a gas inflow tubing, into a treatment probe, and back into the backend component;
throttling the gas through a Joule-Thomson nozzle to rapidly cool the gas;
flowing the gas into the treatment probe for treatment;
directing the gas to flow through the Joule-Thomson nozzle, out of the Joule-Thomson nozzle, into an inner lumen of the treatment probe, and back out through the backend component via a first area within a first lumen in the backend component,
wherein the first area is outside of the Joule-Thomson nozzle,
wherein the Joule-Thomson nozzle extends into a second lumen in the backend component and the second lumen is configured to carry incoming gas of the gas,
wherein a first portion of the second lumen extends into the backend component and a second portion of the second lumen extends outside the backend component, and
wherein the second lumen is wider than the Joule-Thomson nozzle,
wherein a first portion of the Joule-Thomson nozzle that extends into the second lumen is surrounded by another material between the first portion of the Joule-Thomson nozzle and the second lumen,
wherein a second portion of the Joule-Thomson nozzle that extends into the second lumen further extends into the second lumen beyond the other material and ends within the second lumen, and
wherein the backend component is configured to include a choke point portion configured to throttle the incoming gas, flowing from the second lumen and into the Joule-Thomson nozzle, to cool the incoming gas,
wherein the choke point portion is comprised of at least the first portion of the Joule-Thomson nozzle, the second portion of the Joule-Thomson nozzle, the other material, and the first portion of the second lumen, and
wherein the choke point portion throttles the incoming gas via a difference between a first width of the second lumen and a second width of the Joule-Thomson nozzle; and
venting the gas from the backend component.

13. The method of claim 12 further comprising:
selectively turning on or off gas flow at the room temperature tank.

14. The method of claim 12 further comprising:
providing consistent internal pressure via a regulator.

15. The method of claim 12 further comprising providing an ultrasound component for monitoring the cryotherapy.

16. The method of claim 12 further comprising connecting the backend component.

17. The method of claim 12 further comprising generating a freeze-thaw-freeze cycle to freeze a tumor.

18. The method of claim 12 further comprising inserting the treatment probe percutaneously.

19. The method of claim 12 further comprising providing a flange for coupling the treatment probe to the backend component of the device.

20. The method of claim 12 further comprising cooling the $CO_2$ gas to −50° C.

* * * * *